United States Patent [19]
Aehle et al.

[11] Patent Number: 6,017,866
[45] Date of Patent: Jan. 25, 2000

[54] LIPASES WITH IMPROVED SURFACTANT RESISTANCE

[75] Inventors: Wolfgang Aehle; Gijsbert Gerritse; Hermanus B. M. Lenting, all of Delft, Netherlands

[73] Assignee: Genencor International, Inc., Rochester, N.Y.

[21] Appl. No.: 08/732,412

[22] PCT Filed: Apr. 28, 1995

[86] PCT No.: PCT/EP95/01687

§ 371 Date: Oct. 22, 1996

§ 102(e) Date: Oct. 22, 1996

[87] PCT Pub. No.: WO95/30744

PCT Pub. Date: Nov. 16, 1995

[30] Foreign Application Priority Data

May 4, 1994 [EP] European Pat. Off. .............. 94201253

[51] Int. Cl.[7] .............................. C12N 9/20; C12N 1/20; C12N 15/00; C07H 21/04
[52] U.S. Cl. ...................... 510/320; 435/198; 435/252.3; 435/320.1; 435/874; 536/23.2; 536/23.7; 510/305; 510/226; 510/326; 510/392; 530/350
[58] Field of Search .................................. 435/198, 252.3, 435/320.1, 69.1; 536/23.2, 23.7; 510/305, 320, 226, 326, 392; 530/350

[56] References Cited

FOREIGN PATENT DOCUMENTS 0 407 225   1/1991   European Pat. Off. .

*Primary Examiner*—Ponnathapu Achutamurthy
*Assistant Examiner*—Tek Chand Saidha
*Attorney, Agent, or Firm*—Susan Faris; Genencor International, Inc.

[57] ABSTRACT

The present invention provides mutant lipases which retain lipase activity, but have improved surfactant resistance and are thus highly advantageous for use in detergent compositions. Preferred lipases of this type include modified functional forms of a lipase of *Pseudomonas alcaligenes* having one or more amino acid substitutions at or near the surface of the lipase which effect interaction of the hydrophobic portions of surfactant molecules with initiation sites on the enzyme for surfactant denaturation.

17 Claims, 6 Drawing Sheets

FIG._1A

```
GTACCCCTGG CTGGCAGGCG GCAGCCAGGC CCCACAGGGG GAGTCGAGAA ACGCTCCTGT   60

TCCCCTCGGT AACATCCCCT AGGTAATAGC AGAGCCCTTG CCGGCGCTGG CTTTCGTCAC  120

AAACGCCCGT TTAGAGCCTT TGTTCTAATC CACCCCGTTC CTGGCACAGA TCCTGCCCCA  180

CCGAGCCTGC TGAAGTACCG GCCCGGGAAG CGCCGGATGG CTGGATGCAA GGATGGATCA  240

GTGCCCAACC CTTCGCTCGA GAGCAAAAC ATG AAT AAC AAG AAA ACC CTG CTC    293
                                Met Asn Asn Lys Lys Thr Leu Leu
                                -24                 -20
```

| GCC | CTC | TGC | ATC | GGC | AGC | AGT | CTG | CTG | CTG | TCC | GGC | CCA | GCC | GAA | GCC | 341 |
|---|---|---|---|---|---|---|---|---|---|---|---|---|---|---|---|---|
| Ala | Leu | Cys | Ile | Gly | Ser | Ser | Leu | Leu | Leu | Ser | Gly | Pro | Ala | Glu | Ala | |
| -15 | | | | -10 | | | | | | | -5 | | | | | |

| GGC | CTG | TTC | GGC | TCC | ACC | GGC | TAC | ACC | AAG | ACC | AAG | TAC | CCG | ATC | GTC | 389 |
|---|---|---|---|---|---|---|---|---|---|---|---|---|---|---|---|---|
| Gly | Leu | Phe | Gly | Ser | Thr | Gly | Tyr | Thr | Lys | Thr | Lys | Tyr | Pro | Ile | Val | |
| 1 | | | | 5 | | | | | 10 | | | | | 15 | | |

| CTG | ACC | CAC | GGC | CTG | CTC | GGC | TTC | GAC | AGC | ATC | CTC | GGC | GTC | GAC | TAC | 437 |
|---|---|---|---|---|---|---|---|---|---|---|---|---|---|---|---|---|
| Leu | Thr | His | Gly | Leu | Leu | Gly | Phe | Asp | Ser | Ile | Leu | Gly | Val | Asp | Tyr | |
| | | | 20 | | | | | 25 | | | | 30 | | | | |

| TGG | TAC | GGC | ATC | CCG | TCC | TCG | CTG | CGC | TCC | GAC | GGC | GCC | AGC | GTC | TAC | 485 |
|---|---|---|---|---|---|---|---|---|---|---|---|---|---|---|---|---|
| Trp | Tyr | Gly | Ile | Pro | Ser | Ser | Leu | Arg | Ser | Asp | Gly | Ala | Ser | Val | Tyr | |
| | | 35 | | | | | 40 | | | | | 45 | | | | |

| ATC | ACC | GAA | GTC | AGC | CAG | CTC | AAC | ACC | TCC | GAG | CTG | CGC | GGC | GAG | GAG | 533 |
|---|---|---|---|---|---|---|---|---|---|---|---|---|---|---|---|---|
| Ile | Thr | Glu | Val | Ser | Gln | Leu | Asn | Thr | Ser | Glu | Leu | Arg | Gly | Glu | Glu | |
| | 50 | | | | | 55 | | | | | 60 | | | | | |

| CTG | CTG | GAG | CAG | GTG | GAA | GAG | ATC | GCC | GCC | ATC | AGC | GGC | AAG | GGC | AAG | 581 |
|---|---|---|---|---|---|---|---|---|---|---|---|---|---|---|---|---|
| Leu | Leu | Glu | Gln | Val | Glu | Glu | Ile | Ala | Ala | Ile | Ser | Gly | Lys | Gly | Lys | |
| 65 | | | | 70 | | | | 75 | | | | | | 80 | | |

| GTC | AAC | CTG | GTC | GGC | CAC | AGC | CAT | GGC | GGC | CCG | ACC | GTC | CGC | TAC | GTG | 629 |
|---|---|---|---|---|---|---|---|---|---|---|---|---|---|---|---|---|
| Val | Asn | Leu | Val | Gly | His | Ser | His | Gly | Gly | Pro | Thr | Val | Arg | Tyr | Val | |
| | | | | 85 | | | | | 90 | | | | | 95 | | |

| GCC | GCC | GTA | CGC | CCG | GAC | CTG | GTG | GCC | TCG | GTG | ACC | AGC | GTC | GGC | GCC | 677 |
|---|---|---|---|---|---|---|---|---|---|---|---|---|---|---|---|---|
| Ala | Ala | Val | Arg | Pro | Asp | Leu | Val | Ala | Ser | Val | Thr | Ser | Val | Gly | Ala | |
| | | 100 | | | | | 105 | | | | | 110 | | | | |

| CCG | CAC | AAG | GGC | TCG | GAC | ACC | GCC | GAC | TTC | ATC | CGC | CAG | ATC | CCC | CCG | 725 |
|---|---|---|---|---|---|---|---|---|---|---|---|---|---|---|---|---|
| Pro | His | Lys | Gly | Ser | Asp | Thr | Ala | Asp | Phe | Ile | Arg | Gln | Ile | Pro | Pro | |
| | | 115 | | | | | 120 | | | | | 125 | | | | |

| GGC | TCG | GCC | GGT | GAG | GCG | ATA | GTC | GCC | GGC | ATC | GTC | AAC | GGC | CTG | GGC | 773 |
|---|---|---|---|---|---|---|---|---|---|---|---|---|---|---|---|---|
| Gly | Ser | Ala | Gly | Glu | Ala | Ile | Val | Ala | Gly | Ile | Val | Asn | Gly | Leu | Gly | |
| 130 | | | | | 135 | | | | | 140 | | | | | | |

| GCG | CTG | ATC | AAC | TTC | CTC | TCC | GGC | AGC | TCC | AGC | ACC | AGC | CCG | CAG | AAC | 821 |
|---|---|---|---|---|---|---|---|---|---|---|---|---|---|---|---|---|
| Ala | Leu | Ile | Asn | Phe | Leu | Ser | Gly | Ser | Ser | Ser | Thr | Ser | Pro | Gln | Asn | |
| 145 | | | | | 150 | | | | | 155 | | | | | 160 | |

```
GCC CTG GGC GCC CTC GAA TCG CTC AAC AGT GAG GGC GCC GCC GCC TTC    869
Ala Leu Gly Ala Leu Glu Ser Leu Asn Ser Glu Gly Ala Ala Ala Phe
        165             170             175

AAC GCC AAG TAT CCG CAG GGC ATT CCG ACC AGT GCC TGC GGC GAA GGC    917
Asn Ala Lys Tyr Pro Gln Gly Ile Pro Thr Ser Ala Cys Gly Glu Gly
        180             185             190

GCC TAC AAG GTC AAT GGC GTC AGC TAC TAC TCC TGG AGC GGC ACC AGC    965
Ala Tyr Lys Val Asn Gly Val Ser Tyr Tyr Ser Trp Ser Gly Thr Ser
        195             200             205

CCG CTG ACC AAT GTG CTC GAC GTC AGC GAC CTG CTG CTG GGC GCC AGC   1013
Pro Leu Thr Asn Val Leu Asp Val Ser Asp Leu Leu Leu Gly Ala Ser
        210             215             220

TCG CTG ACC TTC GAC GAG CCC AAC GAC GGC CTG GTC GGG CGC TGC AGC   1061
Ser Leu Thr Phe Asp Glu Pro Asn Asp Gly Leu Val Gly Arg Cys Ser
225             230             235             240

TCG CAC CTG GGC AAG GTG ATC CGC GAC GAC TAC CGG ATG AAC CAC CTC   1109
Ser His Leu Gly Lys Val Ile Arg Asp Asp Tyr Arg Met Asn His Leu
        245             250             255

GAC GAG GTC AAC CAG ACC TTC GGC CTG ACC AGC CTG TTC GAG ACC GAC   1157
Asp Glu Val Asn Gln Thr Phe Gly Leu Thr Ser Leu Phe Glu Thr Asp
        260             265             270

CCG GTC ACC GTG TAC CGC CAG CAG GCC AAC CGC CTC AAA CTG GCC GGC   1205
Pro Val Thr Val Tyr Arg Gln Gln Ala Asn Arg Leu Lys Leu Ala Gly
        275             280             285

CTC TGAGCCATGG ATCGGGGCCC ACGGGCCCCG ATGTTTTCCC CCGCCGAGTC TCGCC   1263
Leu
290
```

HPLC-ANALYSIS OF HYDROLYSIS PRODUCTS

| STEP | CONDITIONS |
|---|---|
| Extraction of Swatch | 5 ml HPLC-eluent |
| HPLC-Conditions<br>    Column<br>    Eluent<br><br>    Pump Speed<br>    Temperature<br>    Detection<br><br>    Retention Time<br>        Triolein<br>        Free Fatty Acid<br>        1,3-diacylglyceride<br>        1,2-diacylglyceride | <br>CP Microspher-Si 100*4.6 mm<br>n-hexane / IPA / Formic Acid<br>    97.5 / 2.5 / 0.25<br>1 ml / min<br>Ambient<br>Refractive Index<br><br><br>1.22<br>1.62<br>2.46<br>3.60 |

EXAMPLE OF HPLC-CHROMATOGRAM

FIG._5

LIPASES WITH IMPROVED SURFACTANT RESISTANCE

This application is a section 371 of PCT/EP/95/01687 filed Apr. 28, 1995.

The present invention relates to methods for modifying lipases in a way that their stability is increased. It relates more specifically to lipases for use in detergent compositions with improved resistance towards surfactants.

Lipases are enzymes capable of hydrolyzing lipids. They are used in a wide range of applications, such as processing of fats and oil, detergent compositions for cleaning purposes and diagnostic reagents.

Extracellular lipases (triacylglycerol acylhydrolases, E.C. 3.1.1.3) are produced by a wide variety of microorganisms. Isolated microbial lipases have for example been disclosed in U.S. Pat. No. 3,950,277. These lipases were obtained from such diverse microorganisms as *Pseudomonas, Aspergillus, Pneumococcus, Staphylococcus, Mycobacterium tuberculosis, Mycotorula lipolytica* and *Sclerotinia*.

Examples of the use of lipases from various microorganisms in detergent compositions are given in for instance EP 463100 (*Pseudomonas pseudoalcaligenes*), EP 0218272 (*Pseudomonas pseudoalcaligenes*), EP 0214761 (*Pseudomonas cepacia*), EP 0258068 (*Thermomyces*) and EP 206390 (*Pseudomonas chromobacter, Pseudomonas fluorescens, Pseudomonas fragi, Pseudomonas nitroreductans, Pseudomonas gladioli, Chromobacter viscosum*).

Especially the *Pseudomonas* lipases have favourable characteristics for the known desired applications of lipases. *Pseudomonas* species have therefore been extensively used for obtaining lipases. Several of the *Pseudomonas lipase* genes have been cloned, thereby enabling increased fermentation yield in production of these lipases in both homologous and heterologous host strains. Examples of *Pseudomonas* species from which cloning of a lipase gene has been reported are: *Pseudomonas cepacia* (EP 331376), *Pseudomonas glumae* (EP 464922), *Pseudomonas alcaligenes* (EP 334462) and *Pseudomonas fragi* (EP 318775). For use as an ingredient in detergent compositions, lipases should desirably be resistant to all other ingredients. It has for example been shown that it is possible to stabilize the lipase from *Pseudomonas glumae* against oxidizing components of a detergent composition by replacing methionines by one of the other 19 possible natural occurring amino acids (EP 407225).

Another document describes the stabilization of the same lipase against proteolytic cleavage by a protease component of a detergent composition (Frenken, L. G. J. et al. Protein Engineering 6 (1993) 637–642).

Another important stability problem is the sensitivity of enzymes towards denaturation by anionic, cationic or nonionic surfactant molecules. Anionic surfactant molecules (e.g. laurylsulphate, dodecylsulphate) are amphiphilic molecules having a hydrophobic aliphatic part and a negatively charged hydrophilic part, such as a sulphonate group. Cationic surfactant molecules contain a positively charged group such as a quarternary ammonium group instead of a negatively charged sulphonate group and in nonionics the hydrophilic part of the molecule is formed by a polar but uncharged group like an alcohol group.

The present invention solves the problem of lack of stability of lipases in the presence of surfactants. In particular, in one aspect, it provides a mutant lipase which is a modified functional form of a natural lipase or functional portion thereof having one or more amino acid substitutions at or near the surface compared to said natural lipase or portion thereof so as to increase surfactant resistance.

One of the mechanisms through which surfactant induced denaturation of proteins in general may be caused is by penetration of the hydrophobic part of the surfactant molecule into the hydrophobic core of the enzyme. This process leads to unfolding of the 3D-structure of the protein and thereby results in irreversible loss of catalytic activity.

We have now found that initiation sites for such a process in a lipase can be blocked or removed by one or a few amino acid substitutions, e.g. produced by site-directed mutagenesis of the corresponding native DNA coding sequence. We have found that it is thus possible to enhance the resistance of lipases to surfactants without substantially altering their other useful properties.

Modified lipases of the present invention are especially advantageous in heavy duty detergents because of the amount and aggressive activity of surfactants present in such compositions. They are also very well suited for use in automatic dishwashing detergents.

Although the present invention is more specifically explained with reference to mutated lipases produced by recombinant DNA technology, it will be clear to the man skilled in the art that one or more necessary amino acid modifications to produce a lipase of the invention may also be effected by chemical modification.

One successful attempt to similarly enhance the resistance of a non-lipase protein, in particular the highly alkaline protease, has been disclosed (DE4106525 and EP-A-0525610). In the case of the highly alkaline protease, it has been shown that replacement of amino acid residues with hydrophobic side chains by amino acid residues with polar or charged side chains or replacement of amino acid residues with small side chains by amino acid residues with more space filling side chains leads to improved stabilization of the enzyme towards anionic surfactants.

It is, however, impossible to transfer such teaching to an enzyme of a completely different class such as a lipase. Often the introduction of amino acid sequence changes in an enzyme leads to changes in activity as well. Moreover, at the atomic level the mechanisms of action of surfactants on subtilisin and lipases are not known and may be completely different. Hence, previous success in increasing surfactant resistance of subtilisin by amino acid substitutions was not predictive of similar success in increasing surfactant resistance of a lipase by the same strategy.

Since subtilisin has no homology with lipases, it is impossible to predict from previous publications on subtilisin which amino acid residues in a lipase could be modified to improve surfactant resistance without destroying activity. Furthermore, other ingredients of a detergent composition may influence what changes can be made to a lipase for use in such a composition without substantially affecting the activity of the enzyme or decreasing its stability.

The inventors for the present invention have found that it is possible to identify initiation sites for surfactant denaturation of a lipase by visually inspecting the surface of the three dimensional structure of the enzyme obtained by X-ray crystallography or molecular modelling techniques. Such initiation sites can, for example, be hydrophobic patches on the surface of the enzyme where the surfactant can attach first with its hydrophobic part and then penetrate into the enzyme hydrophobic core. Such hydrophobic patches can be removed by introducing an amino acid residue with a charged or polar side chain.

Other initiation sites for surfactant denaturation of a lipase are surface cavities of the enzyme. Such cavities must have a diameter of at least 30 nm to enable the hydrophobic part of a surfactant molecule to penetrate via the cavity into the hydrophobic core of the enzyme. Accessibility of cavities of this type to surfactant molecules can be reduced by introducing amino acid side chains with a greater space requirement, which at least partially fill the cavity or cover the entrance. This type of mutation thus prevents denaturation by the hydrophobic part of a surfactant through steric hindrance. If a surface cavity of a lipase which provides an initiation site for surfactant denaturation is surrounded mainly by amino acids with hydrophobic side chains, one can also improve surfactant resistance by replacing these amino acids by amino acids with polar or charged side chains. This type of mutation weakens the hydrophobic contacts between the cavity of the enzyme and the hydrophobic parts of surfactant molecules and thus also reduces the capability of surfactant molecules to penetrate via the cavity into the hydrophobic core of the enzyme.

Another modification strategy according to the invention is modification of the surface charge of a lipase by point mutations. Initial approach of an anionic surfactant molecule to a lipase surface is probably driven by attractive electrostatic interactions between positively charged arginine and lysine side chains at the enzyme surface and the negative part of the surfactant molecule. If there is a hydrophobic patch in proximity to a positively charged amino acid side chain at the enzyme surface, a surfactant molecule, once attracted by the positively charged side chain, can easily penetrate into the enzyme. A remedy according to the invention is replacing such positively charged side chains through point mutations with amino acids having negatively charged side chains or polar but uncharged side chains.

Some of the many possible mutations at the surface of a lipase may also have negative influence on the catalytical efficiency of the enzyme. An identified cavity may, for example, be a solvent channel which is necessary for transportation of water molecules from the outer surface of the enzyme to the active site, where they are required as one of the substrates for the triglyceride hydrolysis reaction. An amino acid substitution in such a cavity could prevent its water transport function and hence destroy activity of the lipase. It is, however, readily possible to test modified lipases for their hydrolyzing activity and select those exhibiting no significant reduction in activity.

The catalytic mechanism of lipases in general depends upon the amphiphilic substrate (a triglyceride) approaching the active site region, which is normally covered by a so called lid and found in the interior part of the lipase. This can probably also happen through hydrophobic channels which are accessible from the surface.

Hydrophobic patches on the surface of a lipase may also be important for interaction of the enzyme with its substrates. It might, for example, be necessary for a lipase to have a specific orientation or contact with the hydrophobic part of a substrate for optimal function. Disturbance of the hydrophobicity pattern of a lipase surface by introduction of a amino acids with polar or charged side chains may thus also influence the observed activity of the modified lipase.

It is therefore surprising that we have been able to identify a number of sites on a lipase molecule which can be modified so as to improve surfactant resistance without substantially reducing the hydrolyzing activity. Moreover, mutant lipases of the invention have been observed to have improved washing performance. The behaviour of an enzyme in washing applications is still unpredictable. It has until now not been possible to confirm why a specific mutation in a detergent enzyme leads to a better washing performance of the mutated enzyme. Better washing performance has been observed to neither correlate with the specific activity of the enzyme nor with improvement of another property of the enzyme such as oxidation stability. It is therefore unexpected that modified lipases according to the invention have been found to have an improved washing performance.

Furthermore, it has been found that mutations that are known to improve the thermostability of enzymes also improve the stability of the enzyme towards anionic surfactant molecules. These are for example modifications which strengthen the hydrophobic interactions in the interior of the protein. The importance of such interactions for enzyme stability has been studied on model systems (J. T. Kellis et al., Nature 333, 784–786 (1988)). It is however never been shown that this type of mutations can have in other enzymes an impact on the stability towards anionic surfactant molecules. Another type of general stabilizing mutations are those which stabilized in a model system in α-helices (L. Serrano et al., Nature 356, 453–455 (1992), Serrano et al., J. Mol. Biol. 227, 544–559 (1992)). Again it has never been proven that these mutations can lead to an enzyme with increased resistance against surfactant molecules in detergent formulations.

We have identified the following residues on the surface of the *Pseudomonas alcaligenes* lipase of Sequence I.D. no. 2 (which corresponds to M21L of *Pseudomonas alcaligenes* M1 (CBS 473.85) and which is presently sold as Lipomax®) which are located in suitable positions with respect to initiation sites for surfactant denaturation to be usefully modified in accordance with the present invention: ILE 15, GLY 29, VAL 30, ARG 41, SER 46, ILE 49, GLU 51, LEU 55, ASN 56, THR 57, LEU 60, LEU 66, VAL 69, ALA 73, VAL 81, PRO 91, THR 92, ARG 94, TYR 95, VAL 96, ALA 97, VAL 99, LEU 103, VAL 104, ALA 112, LYS 115, ALA 120, ILE 123, ARG 124, PRO 127, ILE 135, VAL 136, ILE 139, VAL 140, PRO 158, LEU 162, LEU 165, SER 167, GLY 172, ALA 173, ALA 175, PHE 176, TYR 180, PRO 181, GLN 182, GLY 183, ILE 184, ALA 193, VAL 196, ASN 197, VAL 199, SER 208, PRO 209, LEU 219, LEU 221, GLY 222, SER 224, LEU 235, LEU 243, VAL 246, ILE 247, MET 253, ASN 254, VAL 276, LEU 286, LEU 289, LYS 10, LEU 17, SER 39, ASP 43, SER 46, GLU 59, GLU 63, VAL 69, ALA 73, LYS 78, LYS 80, VAL 84, PRO 91, LYS 195, VAL 196, SER 200, LEU 214, LEU 243, MET 253, LEU 268, THR 271, THR 275, LEU 286.

The amino acids are abbreviated with their one or three lettercode respectively. The code are as follows:

| Alanine | ALA | A, | Arginine | ARG | R, | Asparagine | ASN | N, | Aspartic acid | ASP | D |
|---------|-----|----|----------|-----|----|------------|-----|----|---------------|-----|---|
| Cysteine | CYS | C, | Glutamine | GLN | Q, | Glutamic acid | GLU | E, | Glycine | GLY | G |
| Histidine | HIS | H, | Isoleucine | ILE | I, | Leucine | LEU | L, | Lysine | LYS | K |
| Methionine | MET | M, | Phenylalanine | PHE | F, | Proline | PRO | P, | Serine | SER | S |
| Threonine | THR | T, | Trytophane | TRP | W, | Tyrosine | TYR | Y, | Valine | VAL | V |

The nomenclature used for the mutations is as follows K10E means the replacement of the lysine (LYS) at position 10 by a glutamic acid (GLU). Multiple mutants are designated as follows. K10E/K8OR means the replacement of lysine (LYS) at position 10 by glutamic acid (GLU) plus the replacement of lysine (LYS) at position 80 by arginine (ARG).

Having regard to the above-noted amino acid residues of Sequence I.D. no. 2 substitutions which may, for example, be considered are replacement of amino acid residues with a small uncharged aliphatic side chain, e.g. alanine, by an amino acid residue with a larger non-polar side chain, e.g. replacement of alanine by valine, leucine or phenylalanine. Where it is desired to increase non-polar side chain size at an appropriate selected position in a lipase, this will be done having regard to the following ordering of non-polar amino acids on the basis of increasing side chain size: ala <pro<val<leu<ile<met<phe<trp. Such ordering is on the basis of accessible surface area of the amino acid side chains as published by S. Miller et al. in J. Mol. Biol. 196 (1987) 641–656. Aliphatic residues amongst the above-noted amino acid residues of Sequence I.D. no. 2 may also be replaced by amino acid residues with uncharged polar groups like serine, threonine, asparagine, glutamine, cysteine or tyrosine or by amino acid residues with charged polar side chains like lysine, arginine, histidine, glutamic acid and aspartic acid. In accordance with the present invention, uncharged polar amino acid residues of Sequence I.D. no. 2 identified above may either be replaced by more space filling uncharged polar residues in the increasing order of size ser<thr<cys<asn<gin<tyr or by charged amino acids like glutamic acid, aspartic acid, histidine, lysine and arginine. Having regard again to the above-noted amino acid residues of Sequence I.D. no. 2, those amino acid residues with positively charged side chains like arginine, histidine and lysine may be replaced by amino acid residues with polar groups like serine, asparagine, glutamine, threonine and tyrosine or by amino acid residues with negatively charged side chains like aspartic acid and glutamic acid.

Consideration of such substitutions in Sequence I.D. no.2 led to selection of the following sub-set of amino acid positions for special consideration: LYS 10, LEU 17, SER 39, ASP 43, SER 46, GLU 59, GLU 63, VAL 69, ALA 73, LYS 78, LYS 80, VAL 84, PRO 91, LYS 195, VAL 196, SER 200, LEU 214, LEU 243, MET 253, LEU 268, THR 271, THR 275, LEU 286. Particularly preferred mutant lipases of the present invention are variants of the *Pseudomonas alcaligenes* lipase of Sequence I.D. no. 2 having at least one of the following amino acid substitutions:

LYS 10 GLU, LEU 17 GLN, SER 39 ALA, ASP 43 GLY, SER 46 CYS, GLU 59 GLY, GLU 63 GLY , VAL 69 ALA, ALA 73 LEU, LYS 78 GLU, LYS 80 ARG, VAL 84 ILE, PRO 91 LEU, LYS 195 GLU, VAL 196 GLU, SER 200 ARG or GLY, LEU 214 HIS, LEU 243 TYR, MET 253 TYR, LEU 268 ARG or GLN or PRO, THR 271 ILE, THR 275 ASN, LEU 286 ARG.

It will be clear to the man skilled in the art that an equivalent modification may be made in a lipase having homology, e.g. 70% or more homology, to the lipase of *Pseudomonas alcaligenes* to again obtain a functional lipase with improved surfactant resistance. Such modifications can be made based on alignment of the *P. alcaligenes* lipase amino acid sequence as, for instance, in Misset et al. Protein Engineering 7, 523–529 (1994).

The above teaching as regards modification of the *P. alcaligenes* lipase may thus be readily extended to lipases produced by other members of the *Pseudomonas* genus such as the lipases of *P. aeruginosa, P. glumae, P. plantarii, P. pseudoalcaligenes* and *P. cepacia.* The present invention also extends to functional variants of, for example, the lipases of *Bacillus subtilis, Bacillus Pumilis* and *Humicola lanuginosa.* For the purpose of the present invention, a lipase chosen for modification in accordance with the above teaching may be selected from complete naturally-occuring lipases, enzymatically active fragments of lipases and functional derivatives thereof.

In further aspects, the present invention additionally provides means for producing modified lipases as hereinbefore described by recombinant DNA technology. Thus the invention extends to recombinant DNAs encoding a modified lipase of invention, including such DNAs in the form of expression vectors wherein the coding sequence for the modified lipase is operably linked to control sequences for expression, and transformed cells containing such DNAs.

As hereinbefore indicated, site directed mutagenesis is one way in which the lipase coding sequence for a recombinant DNA of the invention may be obtained, but alternative methods will be known to the man skilled in the art. Site-directed mutagenesis for the purpose of the present invention may be performed in conventional manner using a variety of known techniques.

Figure 4:
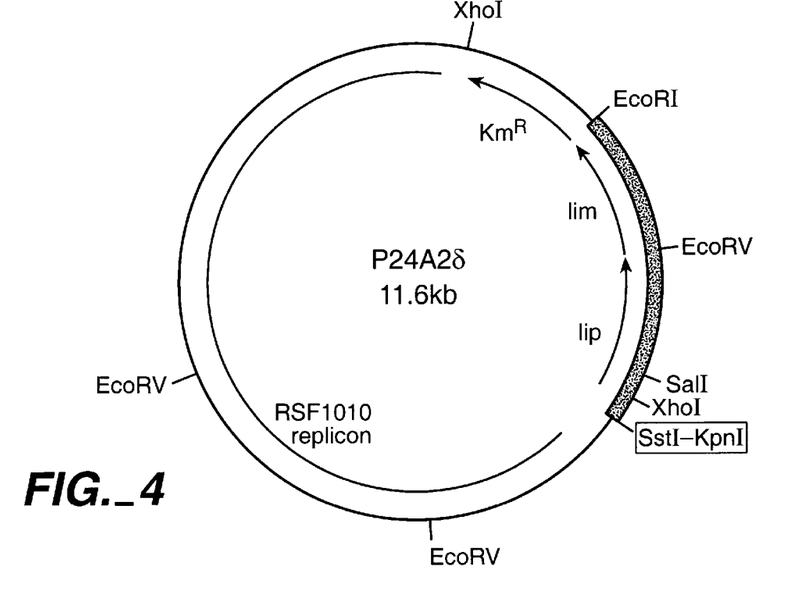
FIG. 4 shows a suitable vector for the expression of a mutant lipase of the invention derived from the *P. alcaligenes* lipase such as the lipase negative *P. alcaligenes* strain Ps600.
Figure 5:
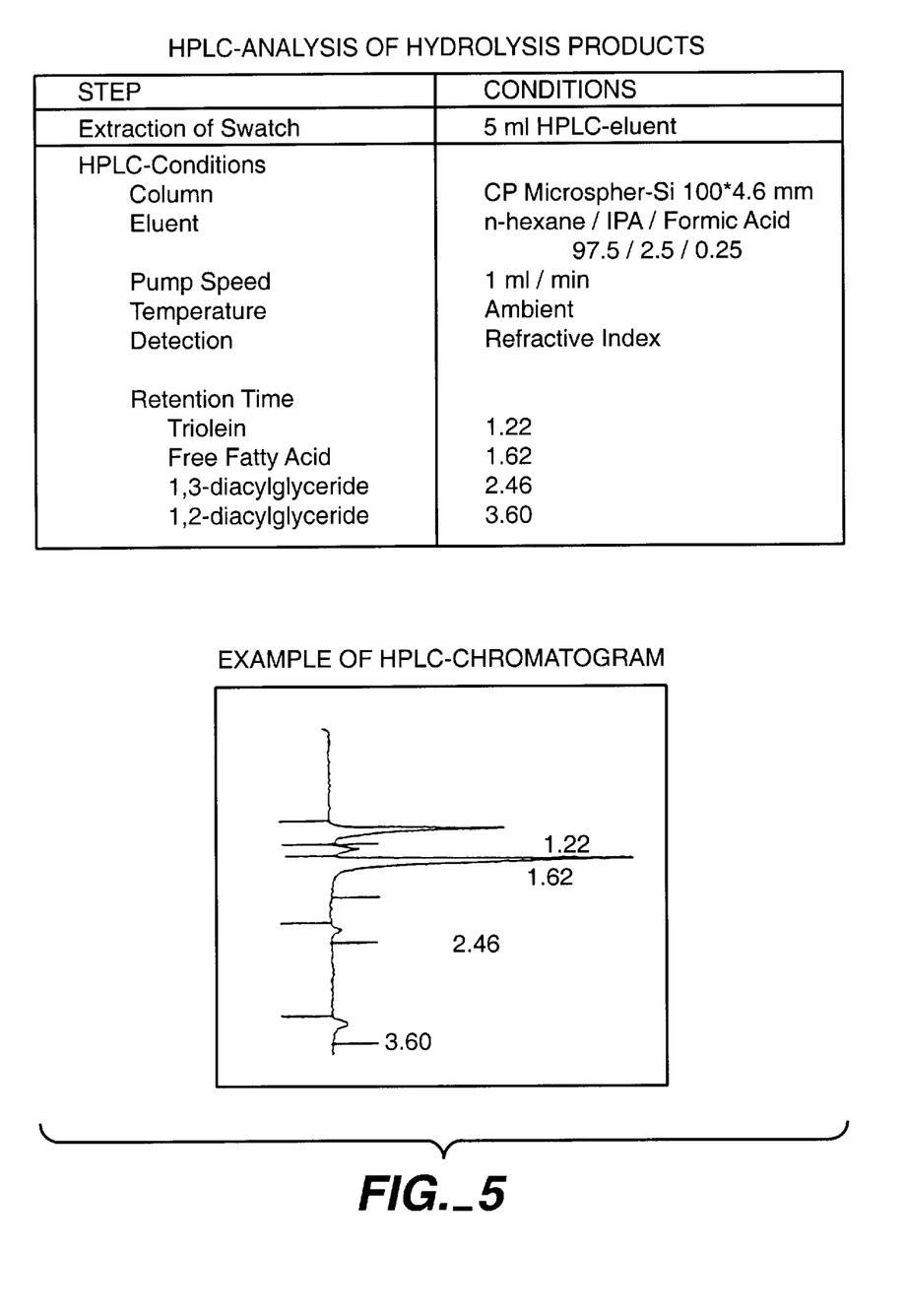
FIG. 5 shows an HPLC test of the activity of a modified lipase according to the invention. The observed retention times for triolein, free fatty acid, 1,3-diacylglyceride and 1,2-diacylglyceride were 1.22 mins, 1.62 mins, 2.46 mins and 3.6 mins respectively.

Those skilled in the art of recombinant technology will also appreciate how to select vectors and host cells to express a mutant lipase of the invention. Suitable vectors to express such lipases are broad host range vectors, preferably derivatives of RSF 1010, especially vector p24 A 2 a (see FIG. 4) or a functional equivalent thereof.

Suitable cells to express lipases according to the invention are *Pseudomonas* cells, preferably *P. alcaligenes* cells, especially cells of a lipase negative *P. alcaligenes* derivative. The lipase gene of *P. alcaligenes* may be inactivated by conventional techniques. In the examples below, preparation of one particular lipase-deficient strain of *P. alcaligenes* designated PS600 is described. It will be appreciated however that the same strategy may be used to prepare other lipase-deficient Pseudomonas strains suitable as hosts for production of lipases of the present invention.

Thus, in a further aspect, the present invention provides a method of preparing a mutant lipase as hereinbefore described which comprises culturing host cells, e.g. lipase-deficient *P. alcaligenes* cells, containing a recombinant DNA capable of directing expression of the desired lipase in said cells, preferably an expression vector, under conditions whereby said lipase is produced.

Part of the invention is, of course, also the use of a mutant lipase as hereinbefore described in the formulation of a detergent compositions as well as the resulting detergent composition per se. Such a detergent composition will contain, in addition to a lipase of the invention, a number of conventional detergent ingredients. Detergent powders generally contain builders (e.g. zeolite, phosphate), surfactants (e.g. anionic, nonionic), polymers (e.g. acrylic), bleach precursors (e.g. borate), bleach activators, structurants (e.g. silicate) and pH adjusting compounds (e.g. alkali). Detergent liquids generally contain surfactants (e.g. anionic, nonionic), bleach precursors (e.g. borate), bleach activators and pH adjusting compounds (e.g. alkali). Other ingredients including enzymes other than lipases (e.g. a protease, a-amylase), organic acids, inorganic salts and softeners may also be incorporated into such compositions.

EXAMPLES

Introduction of mutations by site directed mutagenesis

Figure 1:
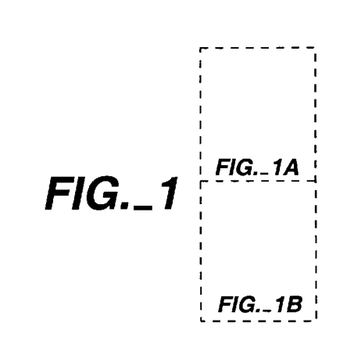
FIG. 1 depicts the amino acid sequence (SEQ ID NO:2) and the DNA sequence (SEQ ID NO:1) of the M21L lipase from *P. alcaligenes*. The preferred amino acid positions for substitutions in accordance with the invention are underlined.
Figure 1B:
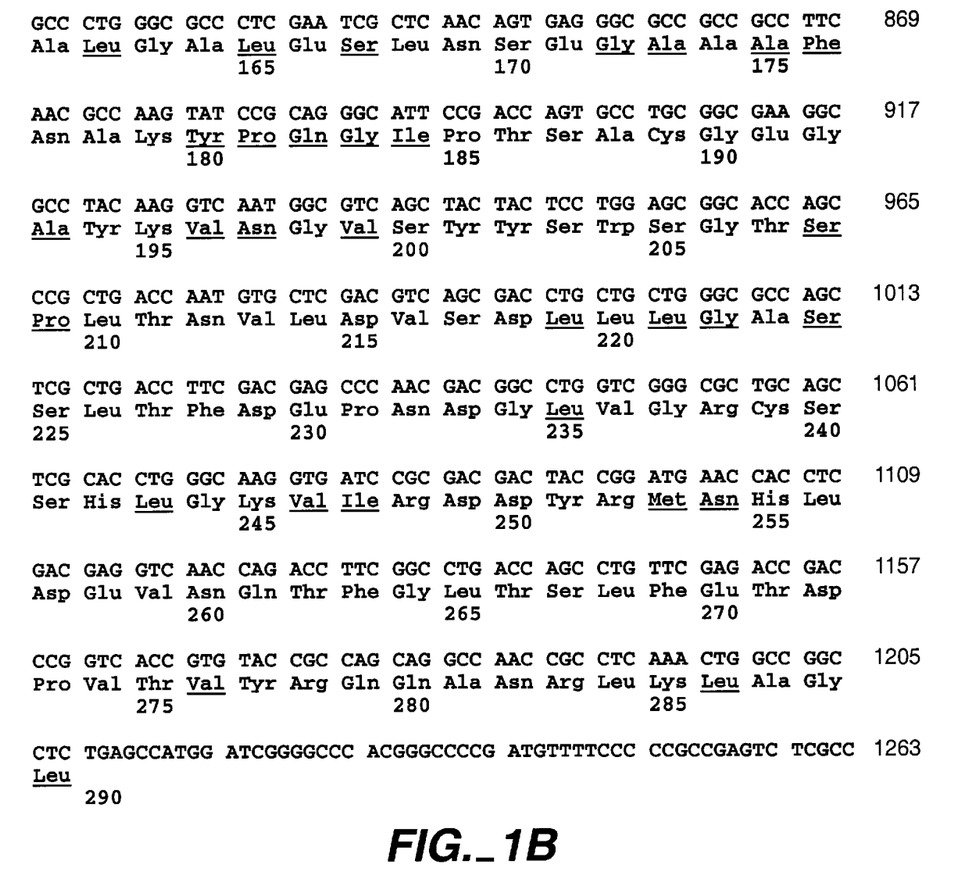
Figure 2:
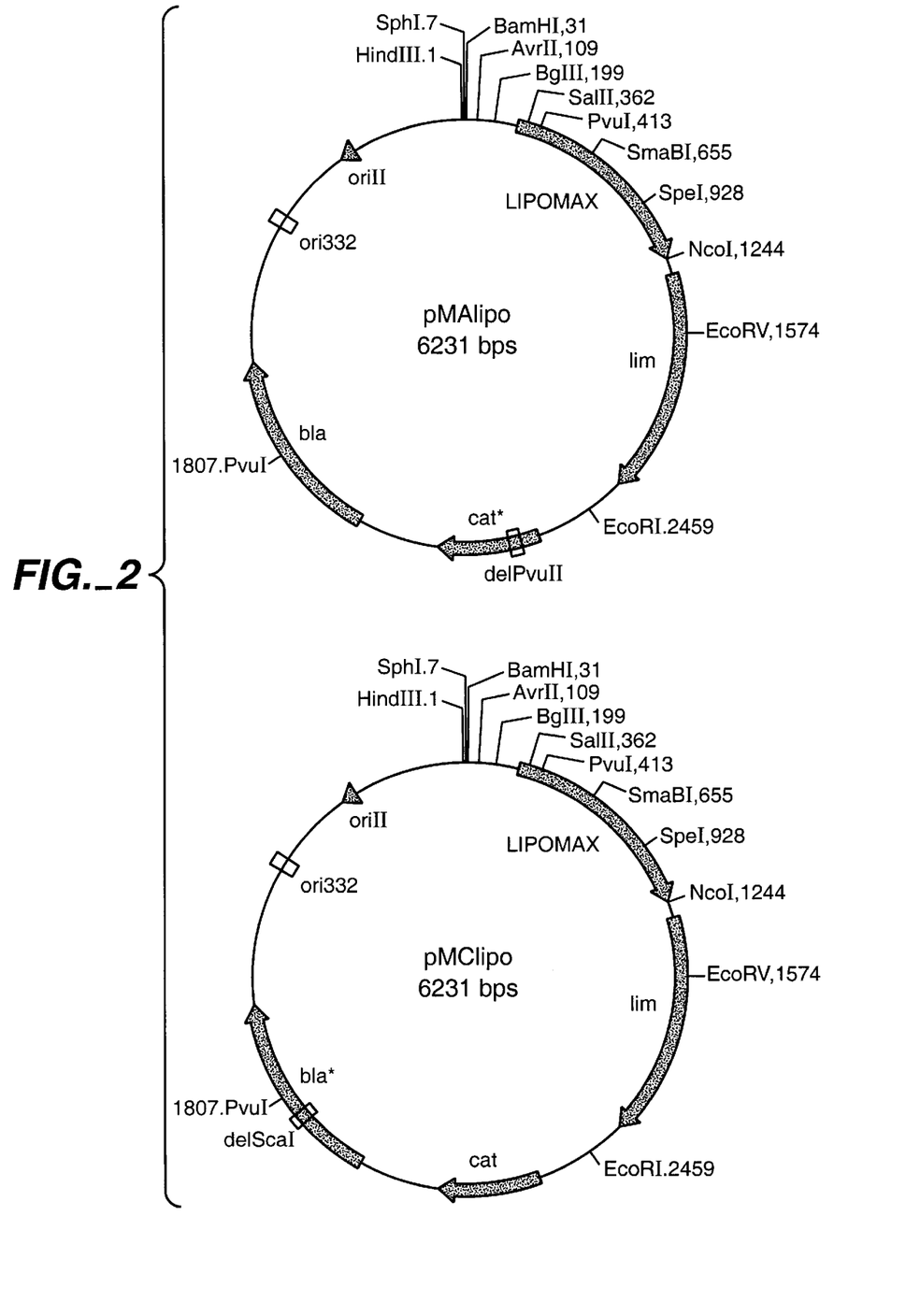
FIG. 2 shows the twin vectors constructed for carrying out site directed mutagenesis of the *P. alcaliaenes* lipase gene in *E. coli*.

Mutations were introduced by using the pMA/C mutagenesis system as described in WO91/00353. Into this twin vector system, a 2.4 kb fragment containing both lipase and lipase helper gene was cloned. Appropriate restriction sites were introduced into the above mentioned vectors in order to minimize the possibility of secondary mutations. The resulting vectors were called pMAlipo (FIG. 2a) and pMClipo (FIG. 2b).

In order to produce a high amount of the mutant enzyme, the mutant gene was cloned in a multicopy plasmid and transformed into a lipase negative strain of *P. alcaligenes* designated Ps600 as decribed below.

Construction of the lipase negative *P. alcaligenes* strain Ps600.

A suicidal integration plasmid, which is unable to replicate in *Pseudomonas alcaligenes*, but able to replicate in other microorganisms, was used to inactivate the lipase gene in the chromosome of Pseudomonas alcaligenes.

The lipase containing gene fragment was subcloned from plasmid pTMPv18 into plasmid pBR322 (Bolivar et al. Gene 2 (1977) 95–113), which is able to replicate in *E. coli*, but unable to replicate in *Pseudomonas alcaligenes*. Then an internal fragment was deleted from the plasmid. The resulting plasmid was called pBRflank.

*Pseudomonas alcaligenes* M1 (CBS 473.85) was transformed with pBRflank. Since this plasmid is unable to replicate in *Pseudomonas*, tetracycline resistant colonies can only be obtained by integration. Several tetracycline resistant (5 mg/l) colonies were selected. In these strains, the plasmid pBRflank is integrated into the bacterial chromosome by a single recombination event at the 5' or 3' flanking region (FIG. 2a). Due to the fact that these strains still contain a functional lipase gene, they exhibit a lipase positive and tetracycline resistant phenotype. Several strains were selected for further experiments. In order to delete the lipase gene and the plasmid from the chromosome, a second recombination (excision) event has to occur. This can be achieved by growing the strains for several days in BHI (Brain Heart Infusion) medium, in the absence of antibiotics. Then the cells were plated on agar medium containing tributyrin. The colonies containing cells with a lipase negative phenotype were also tested for their inability to grow on selective agar plates. The lipase negative strain thus obtained was designated Ps600.

Figure 3A:
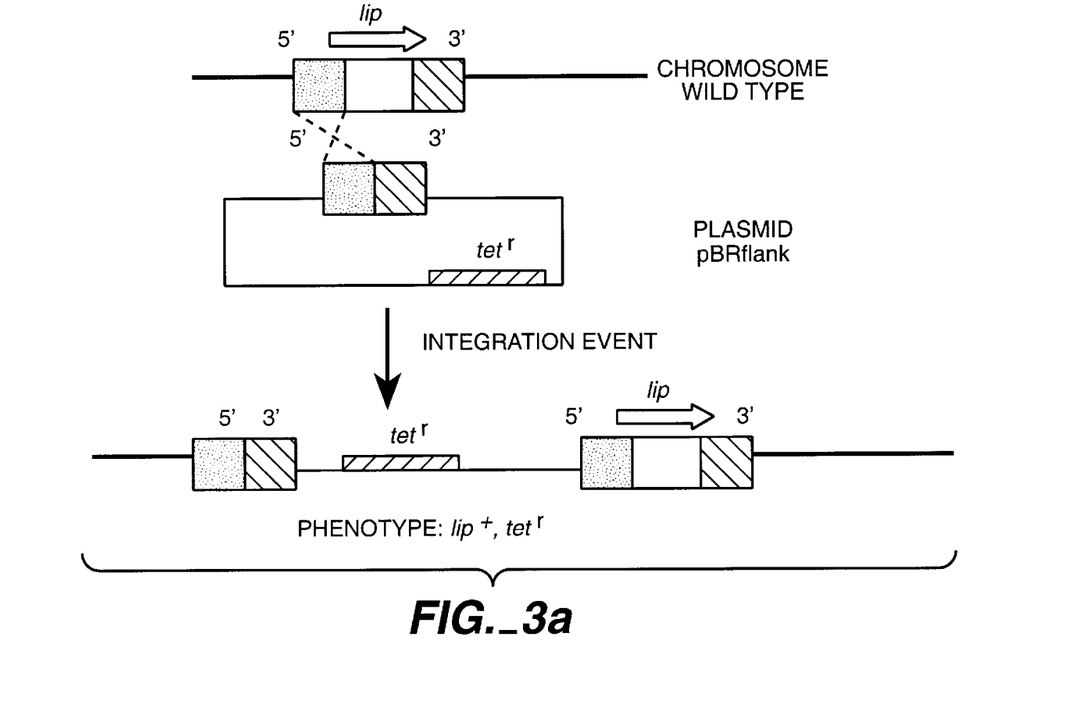
FIG. 3a shows the integration of plasmid pBR-flank into the chromosome of *P. alcaligenes*.
Figure 3B:
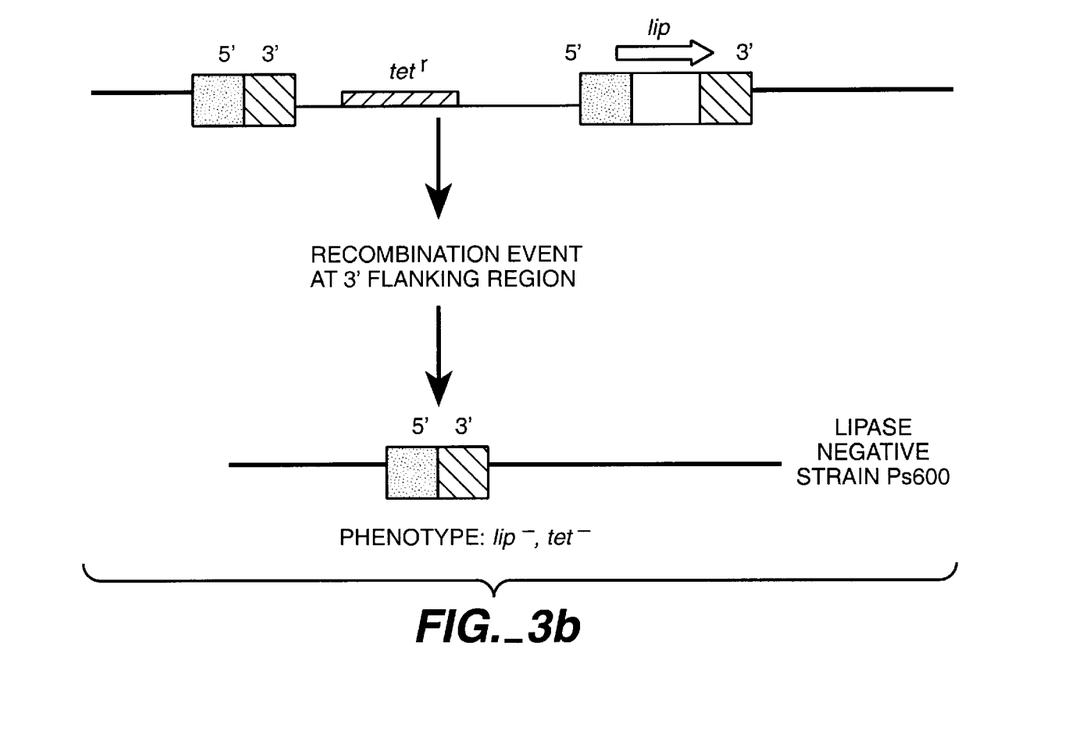
FIG. 3b shows the recombination event to delete the lipase gene from the chromosome of *P. alcaligenes*.

A schematic view of this integration event, followed by a second recombination is shown in FIGS. 3a and 3b.

Production and isolation of the mutant lipases

The strains were grown as described in EP 033462. The lipase protein was then purified from the culture broth as a white powder also as described in EP 033462.

Assay for the determination of lipase activity under washing conditions

The SLM test was used to evaluate alkaline lipase mutants in a washing process. The SLM test uses the same principles as the method developed by T. Hashimoto et al., Yukagaku 34 (1985) 606–612, but the analysis time is drastically reduced.

The method involves using immobilized, non emulsified fat or oil on a fabric as the test stain, extracting the swatch after use in a washing process and analysing solvent extracts for fats and fatty acids formed as a result of lipase activity as well as any residual triglycerides remaining on the textile following the washing process. The quantity of test product left on the swatch appears to be a good measure of the performance of the lipase during the washing process.

The following is a typical example of how the SLM test is preferably carried out:

Polyester swatches are used as the fabric and triolein or purified oil (both products of Sigma, USA) as the substrates. The hydrolysis of triolein can be followed by chromatographic methods after a solvent extraction step.

The washing procedure preferably employed for the SLM test is as follows:

A volume of 80gl containing 10 mg olive oil dissolved in n-Hexane (12.5%) is spotted on a polyester swatch (3×3 cm). The swatch is air dried at room temperature. The washing solution consisting of 10 ml STW (standard tap water: 2 mm Calcium chloride and 0.7 mM Magnesium chloride in distilled water) or detergent dissolved in STW is placed in an Erlenmeyer flask (50 ml) with a ground stopper and kept in a shaking waterbath at 40° C. The washing process is started by adding to the Erlenmeyer flask lipase (40 ILU see below) followed immediately afterwards by the soiled swatch. The flask is shaken for 40 minutes in the water bath. In a control experiment, no lipase is added. After washing, the swatch is rinsed with STW and subsequently dried at 55° C for one hour after which a second washing cycle is carried out. The dried swatch is extracted by rotation in a glass tube containing 5 ml of solvent having the same composition as the eluent used for the chromatographic separation of substrate and products.

The residual amount of triglyceride together with the amount of free fatty acid and 1,2 and 1,3-diacyl-glycerides present in the extraction solution are determined by HPLC.

Equipment and conditions:

Pump: LKB (model 2150)

Detection: Refractive index monitor (Jobin Yvon)

Injection system: Perkin-Elmer Iss-101; 10 μl

Integrator: Spectra Physics, Chromjet

Column: CP-Microspher-Si (chrompack), 100×4.6 mm

Eluent: n-Hexane/Isopropylalcohol/Formicacid: 975:25:2.5 (v/v), 1 ml/min

Temperature: ambient

Under these conditions the retention times of triolein, oleic acid, 1,3- and 1,2-diacylglyceride are (approximately)

1.2, 1.6, 2.4 and 3.6 minutes, respectively. The peak areas or peak heights are measured. They are a measure of the recovery of triolein, oleic acid, 1,3- and 1,2-diacylglyceride after extraction from the swatch. The recovery of triglyceride after extraction from an unwashed swatch is taken as 100%. Under the conditions described above the ratio of the refractive index responses between olive oil, oleic acid, 1,2- and 1,3-diacylglyceride were found to be 1.00, 0.98, 2.10 and 1.30, respectively, on the basis of peak height.

Assay for the determination of lipase activity

Activities of the chosen starting lipase and mutants of the invention, expressed as ILU'S, were determined on the basis of hydrolysis of olive oil. The hydrolysis was measured at 30° C., in a pH-stat containing 10% olive oil in a 0.4 mM Tris buffer pH 9 in the presence of 20 mM sodium chloride and 20 mM calcium chloride. One ILU is defined as the amount of enzyme needed for the release of one gmole fatty acid per minute under the conditions of the test.

Determination of lipase specific activity

The specific activity of wild type and mutant lipases was determined using the activity assay previously mentioned and the BCA (bicinchoninic acid) protein assay as commercialised by Pierce (Rockford, Ill. USA) for the quantification of the protein content (using bovine serum albumin as the standard protein).

Preparation of an enzyme solution for stability tests

A suitable amount of lipase powder was dissolved in 0.1% (w/v) Triton X-100/0.1 M NaCl/1 mM $CaCl_2$ to give a final enzyme concentration of approximately 4 mg/ml. After stirring for 2–3 hours at 4° C. the solid precipitate was removed by centrifugation.

20 ml of the centrifugation supernatant was dialysed against 10 l of a solution of 0.1% (w/v) Triton X-100/0.1M NaCl/1 mM $CaCl_2$ using a Spectra/Por MWCO 3500 membrane during 16–20 hours. 2 ml of this enzyme solution was added to 18 ml acetone, well mixed and kept for 1 hour at −20° C. to precipitate the enzyme.

The solution was centrifugated and the pellet washed once with 15 ml ice cold acetone. The pellet was then dissolved in 0.1% (w/v) Triton X-100/0.1M NaCl/1 mM $CaCl_2$ to achieve a final enzyme concentration of 2 mg/ml.

Determination of stability against the surfactant sodium laurylsulfate (LAS)

0.5 ml of the prepared enzyme solution was added to 0.25 ml Tris/HCl buffer pH 8.0, 0.15 ml 1M NaCl and 0.6 ml Milli Q water. This solution was preincubated at 40° C. After 5 min 0.5 ml 10 mM LAS of 40° C. was added and the whole solution was incubated at 40° C. Samples of 0.1 ml were taken after 0, 5, 10, 20, 30 and 45 minutes of incubation and added to 1 ml 0.15M Tris/HCl/2.7 mM $CaCl_2$ pH 7.8 at 0° C.

The residual activity was than determined with the para-Nitrophenylacetate method as described by V. K. Antonov at al., Biochimie 70 (1988), 1235–1244. The data were tentatively fitted to a simple model assuming a first order irreversible denaturation process (i.e. $A=A_0*e^{-kt}$) using the program Grafit (Leatherbarrow, R. J. (1990) *GraFit* Version 2.0, Erithacus Software Ltd, Staines U.K.) giving the rate constant of this process. The half-life was calculated from the rate constant using the equation t½=ln2/k.

Determination of stability of the enzymes against heavy duty liquid detergents (HDL)

A typical US-type liquid detergent without enzymes was diluted approximately 4 times (1 g HDL+3 g Milli Q water). 1.2 ml of the diluted detergent was preincubated at 40° C. After 5 minutes 0.3 ml of the the prepared enzyme solution was added to the diluted HDL. The whole solution was incubated at 40° C. Samples of 0.1 ml were taken after 0, 15, 30, 60, 90 and 120 minutes of incubation and added to 1 ml Milli Q water at 0° C.

The residual activity was than determined with the para-Nitrophenylacetate method as described by V. K. Antonov at al., Biochimie 70 (1988), 1235–1244.

The data were tentatively fitted to a simple model assuming a first order irreversible denaturation process (i.e. $A=A_0*e^{-kt}$) using the program Grafit (Leatherbarrow, R. J. (1990) GraFit Version 2.0, Erithacus Software Ltd, Staines U.K.) giving the rate constant of this process. The half-life was calculated from the rate constant using the equation t½=ln2/k.

Example 1

Determination of the specific activity of different mutant lipases.

The specific activity of different mutant lipases were determined using the BCA and pH-stat activity assay method as described herein before.

TABLE 1

Specific activity of different mutant lipases

| lipase | specific activity [ILU/μg protein] |
|---|---|
| Lipomax ® | 6.4 |
| K10E | 7.3 |
| K10E/K80R | 6.9 |
| S39A | 6.1 |
| D43G | 5.7 |
| S46C/V84I | 3.2 |
| K78E | 6.3 |
| P91L | 6.2 |
| K195E/L268Q | 7.2 |
| V196E | 5.6 |
| S200G | 7.1 |
| L214H | 6.1 |
| L243Y | 0.006 |
| M253W | 6.5 |
| L268R | 6.5 |
| L268P | 6.7 |
| L268Q | 7.1 |
| T271I | 6.8 |
| T275N | 17.2 |
| S200R/L286R | 11.6 |

As can be seen in Table 1, the specific activities of the mutant lipases are about Lipomax®. Surprisingly T275N and S200R/L286R show a higher specific activity.

By mutant lipase in Example 1, 2 and 3 is meant variants of the *Pseudomonas alcaligenes* lipase of sequence I.D. No. 2.

Example 2

Determination of the half-life of different mutant lipases.

TABLE 2 with half-life from LAS stability tests:

| lipase | Half-life [minutes] |
|---|---|
| Lipomax ® | 10 |
| K10E | 33 |
| K10E/K80R | 36 |

TABLE 2-continued with half-life from LAS stability tests:

| lipase | Half-life [minutes] |
| --- | --- |
| S39A | 28 |
| D43G | 35 |
| S46C/V84I | 99 |
| K78E | 25 |
| P91L | 33 |
| K195E/L268Q | 16 |
| V196E | 11 |
| S200G | 6 |
| L214H | 72 |
| M253W | 2 |
| L268R | 27 |
| L268P | 24 |
| L268Q | 16 |
| T271I | 21 |
| T275N | 32 |

The half-life of different mutant lipases were determined using a method described hereinbefore. Almost all mutant showed improved stability for anionic surfactants under these conditions compared to Lipomax®.

Example 3

Determination of the half life of different mutant lipases

TABLE 3 for example with improved HDL stability:

| lipase | Half-life [minutes] |
| --- | --- |
| Lipomax ® | 28 |
| K10E | 25 |
| K10E/K80R | 34 |
| S39A | 32 |
| D43G | 41 |
| S46C/V84I | 32 |
| K78E | 12 |
| K195E/L268Q | 2 |
| V196E | 30 |
| S200G | 31 |
| L214H | 31 |
| L268P | 115 |
| L268Q | 29 |
| T271I | 60 |
| T275N | 57 |

The half-life of different mutant lipases were determined using methods described before.

Almost all mutants showed improved stability against typical commercially liquid detergent compositions compared to Lipomax®.

Example 4

Lipase activity of mutants of lipase M1 (CBS 473.85) under application conditions (SLM test).

The SIM test using lipase M1 mutants M21L, M21L/K78E and M21L/Vl96E was carried out as described herein before. The following conditions were used in this single cycle washing test:

standard tap water (STW)

detergent is Ariel Ultra™ (2 g/l)

lipase dosage as indicated.

Ariel Ultra™ is a product of Procter & Gamble and is commercially available. This detergent contains neither a protease nor a lipase.

TABLE 4

| Lipase mutant | conc. (µg/ml) | residual intact triglyceride |
| --- | --- | --- |
| none | — | 98.2 |
| M21L (= Lipomax ®) | 0.1 | 87.7 |
| M21L | 0.2 | 82.6 |
| M21L | 0.4 | 76.3 |
| M21L | 0.8 | 65.6 |
| M21L/K76E | 0.1 | 82.7 |
| M21L/K78E | 0.2 | 78.2 |
| M21L/K78E | 0.4 | 71.6 |
| M21L/K78E | 0.8 | 60.8 |
| M21L/V196E | 0.1 | 85.4 |
| M21L/V196E | 0.2 | 81.4 |
| M21L/V196E | 0.4 | 70.2 |
| M21L/V196E | 0.8 | 64.6 |

From this Table it appears that the lipases used show their lipolytic properties on textile in the presence of detergent. These results clearly demonstrate that both mutants of Lipomax® are more active than the M21L lipase (Lipomax®) mutant under these relevant application conditions when added on the same weight base.

Example 5

Wash performance of M21L and K21L/K78E mutant lipases in a washing process according to the Laundr-o-meter test using a European detergent The wash performance of the above mentioned mutant lipases was determined in the Laundr-o-meter test under the following conditions:

2.5 mM calcium chloride waterhardness detergent is Ariel Ultra™ (5 g/l)

0.75 mg/l Maxacal® lipase dosage as indicated wash temperature is 40° C.

wash cycle is 40 min.

monitor is lipstick stain LS2 on polyester/cotton from WFK-Testgewebe, Krefeld, Germany Ariel Ultra™ is a commercially available powder detergent from Procter & Gamble. The detergent base used contains no protease or lipase.

Figure 6:
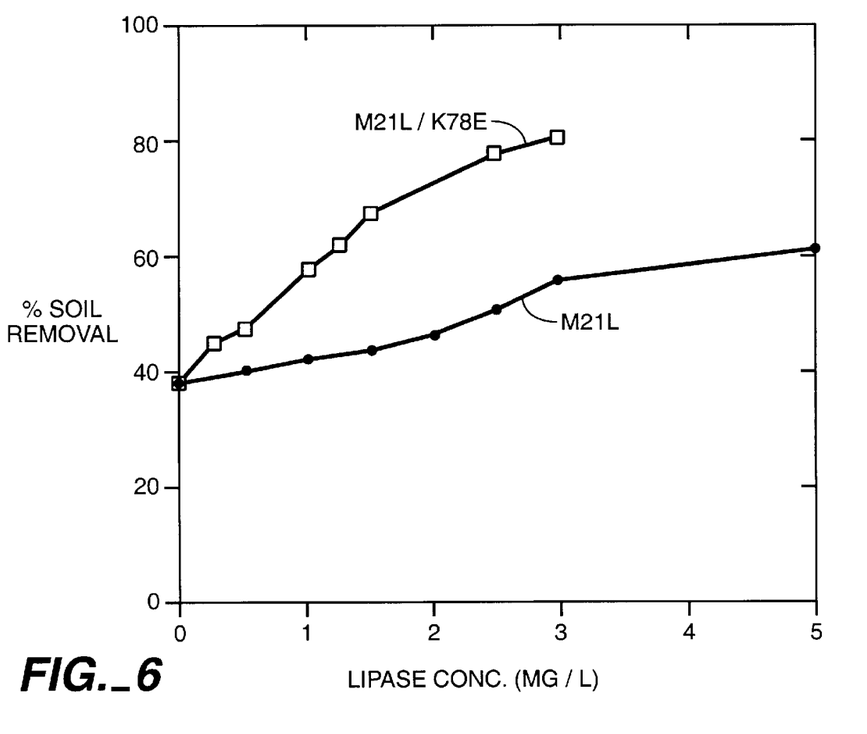
FIG. 6 shows the effect of lipase addition on lipstick removal after one wash cycle.

FIG. 6 clearly demonstrates that the additional K78E mutation can be held responsible for the improved wash performance of this Lipomax®.

Example 6

Wash performance of M21L and K21L/X78E mutant lipases in a washing process according to the Laundr-o-meter test using a USA detergent.

The wash performance of the above mentioned mutant lipases was determined in the presence of Tide™ (dosage 1.3 g/l) in the system as described in Example 5 with one exception: the waterhardness used is 0.75 mM calciumchloride and 0.25 mM magnesiumchloride.

Tide™ is a commercially available powder detergent from Procter & Gamble. The detergent base used contains no protease or lipase.

TABLE 5

| lipase dosage | percentage soil removal | |
|---|---|---|
| (mg/l sud) | M21L | M21L/K78E |
| — | 32.0 | 32.0 |
| 0.7 | 38.8 | 56.3 |
| 1.25 | 42.9 | 66.3 |
| 2.50 | 52.3 | 72.4 |

From this Table it is clear that also in the presence of Tide™ the M21L/K78E mutant lipase has improved performance characteristics over Lipomax®.

Example 7

Wash performance of M21L and M21L/K78E mutant lipases in a washing process according to the Laundr-o-meter test using butterfat stain as monitor.

The wash performance of the above mentioned mutant lipases was determined in the presence of both Ariel Ultra™ and Tide™. The conditions used are described in Examples 5 (Ariel Ultra™) and 6 (Tide™). The LS4 butterfat test monitor on polyester was obtained from the Center for Testmaterials, Vlaardingen, Holland.

TABLE 6

The effect of lipase addition to both Ariel Ultra ™ and Tide ™ on butterfat removal after one wash cycle.

| | dosage | percentage butterfat removal | |
|---|---|---|---|
| lipase | (mg/l) | Ariel Ultra ™ | Tide ™ |
| — | — | 25.8 | 50.8 |
| M21L | 1.25 | 25.8 | 53.5 |
| M21L | 2.50 | 25.5 | 54.0 |
| M21L/K78E | 1.25 | 29.6 | 64.6 |
| M21L/K78E | 2.50 | 31.6 | 65.1 |

This Table shows again that using butterfat as monitor the M21L/K78E mutant lipase exhibits improved wash performance characteristics when compared with the M21L mutant lipase (Lipomax®).

Example 8

Wash performance of M21L and M21L/V196E mutant lipases in a washing process according to the Laundr-o-meter using lipstick as monitor.

The wash performance of the above mentioned mutant lipases was determined in the presence of Ariel Ultra™ (5 g/l) or Tide™ (1 g/l) under the conditions as mentioned in the Examples 5 (Ariel Ultra™) and 6 (Tide™).

TABLE 7

The effect of lipase addition on lipstick removal in the presence of Ariel Ultra ™ or Tide ™.

| | dosage | percentage lipstick removal | |
|---|---|---|---|
| lipase | (mg/l) | Ariel Ultra ™ | Tide ™ |
| M21L | — | 31.5 | 58.1 |
| M21L | 1.25 | 39.5 | 75.5 |
| M21L | 2.50 | 43.4 | 76.9 |
| M21L/V196E | 1.25 | 38.9 | 82.3 |
| M21L/V196E | 2.50 | 59.5 | 78.0 |

From this Table it can be concluded that the double mutant exhibits an improved wash performance when compared with the single (M21L) mutant lipase, especially in the presence of Ariel Ultra™ at high enzyme dosage.

We claim:

1. A mutant lipase, which is a modified functional form of a natural lipase selected from a *Pseudomonas* species having (i) an amino acid sequence of SEQ ID NO:2; or (ii) an enzymatically active fragment of (i) and said modified functional form having at least one of the following amino acid substitutions in SEQ ID NO:2: LYS 10, ILE 15, LEU 17, GLY 29, VAL 30, SER 39, ARG 41, ASP 43, SER 46, ILE 49, GLU 51, LEU 55, ASN 56, THR 57, GLU 59, LEU 60, GLU 63, LEU 66, VAL 69, ALA 73, LYS 78, LYS 80, VAL 81, VAL 84, PRO 91, THR 92, ARG 94, TYR 95, VAL 96, ALA 97, VAL 99, LEU 103, VAL 104 ALA 112, LYS 115, ALA 120, ILE 123, ARG 124, PRO 127, ILE 135, VAL 136, ILE 139, VAL 140, PRO 158, LEU 162, LEU 165, SER 167, GLY 172, ALA 173, ALA 175, PHE 176, TYR 180, PRO 181, GLN 182, GLY 183, ILE 184, ALA 193, LYS 195, VAL 196, ASN 197, VAL 199, SER 200, SER 208, PRO 209, LEU 214, LEU 219, LEU 221, GLY 222, SER 224, LEU 235, LEU 243, VAL 246, ILE 247, MET 253, ASN 254, LEU 268, THR 271, THR 275, VAL 276, LEU 286, and LEU 289; wherein the surface resistance of the mutant lipase is increased compared to said natural lipase.

2. The mutant lipase according to claim 1, wherein the mutant lipase is a modified functional form of a natural lipase selected from a *Pseudomonas* species having the amino acid sequence of SEQ ID NO:2 and including at least one of the amino acid substitutions.

3. The mutant lipase according to claim 1 further comprising an additional substitution in SEQ ID NO:2 at the amino acid position MET 21.

4. The mutant lipase according to claim 1, wherein the modified functional form of the lipase is from *Pseudomonas alcaligenes*.

5. The mutant lipase according to claim 1, wherein the Pseudomonas species are selected from the group consisting of *P. pseudoalcaligenes, P. aeruginosa, P. plantarii,* and *P. cepacia*.

6. The mutant lipase according to claim 1, wherein at least one amino acid substitution is selected from the following positions, LYS 10, LEU 17, SER 39, ASP 43, SER 46, GLU 59, GLU 63, VAL 69, ALA 73, LYS 78, LYS 80, VAL 84, PRO 91, LYS 195, VAL 196, SER 200, LEU 214, LEU 243, MET 253, LEU 268, THR 271, THR 275, and LEU 286.

7. The mutant lipase according to claim 6, wherein at least one amino acid substitution is selected from the following positions: LYS 10, SER 39, ASP 43, SER 46, LYS 78, PRO 91, LYS195, VAL196, SER200, LEU214, LEU243, MET253, LEU268, THR 271, and THR 275.

8. The mutant lipase according to claim 6, wherein at least one amino acid substitution is selected from the following positions: LYS 10 GLU, LYS 10 GLU/LYS 80 ARG, SER 39 ALA, ASP 43 GLY, SER 46 CYS/VAL 84 ILE, LYS 78 GLU, PRO 91 LEU, LYS 195 GLU/ LEU 268 GLN, VAL 196 GLU, SER 200 GLY, LEU 214 HIS, LEU 243 TYR, MET 253 TRP, LEU 268 ARG, PRO, or GLN, THR 271 ILE, and THR 275 ASN.

9. A mutant lipase, which is a modified functional form of a natural lipase selected from a Pseudomonas species having an amino acid sequence of SEQ ID NO:2 or an enzymatically active fragment thereof, and having at least one amino acid substitution selected from the following positions, LYS 10, LEU 17, SER 39, ASP 43, SER 46, GLU 59, GLU 63, VAL 69, ALA 73, LYS 78, LYS 80, VAL 84, PRO 91, LYS 195, VAL 196, SER 200, LEU 214, LEU 243, MET 253, LEU 268, THR 271, THR 275, and LEU 286 wherein the surface resistance of the mutant lipase is increased compared to said natural lipase.

10. The mutant lipase according to claim 9 wherein the amino acid substitution is selected from the following positions in SEQ ID NO:2, LYS 10 GLU, LEU 17 GLN, SER 39 ALA, ASP 43 GLY, SER 46 CYS, GLU 59 GLY, GLU 63 GLY, VAL 69 ALA, ALA 73 LEU, LYS 78 GLU, LYS 80 ARG, VAL 84 ILE, PRO 91 LEU, LYS 195 GLU, VAL 196 GLU, SER 200 ARG or GLY, LEU 214 HIS, LEU 243 TYR, MET 253 TYR, LEU 268 ARG or GLN or PRO, THR 271 ILE, THR 275 ASN, and LEU 286 ARG.

11. The mutant lipase according to claim 9 or claim 10 further comprising an additional substitution in SEQ ID NO:2 at the amino acid position MET 21.

12. The mutant lipase according to claim 9, wherein the mutant lipase is selected from the species *P. alcaligenes, P. pseudoalcaligenes, P. aeruginosa, P.glumae, P. plantarii,* and *P. cepacia.*

13. A mutant lipase, which is a modified functional form of a natural lipase selected from a Pseudomonas species having (i) an amino acid sequence of SEQ ID NO:2; or (ii) an enzymatically active fragment of (i) and said modified functional form having at least one of the following amino acid substitutions in SEQ ID NO:2: LYS 10 GLU, LEU 17 GLN, SER 39 ALA, ASP 43 GLY, SER 46 CYS, GLU 59 GLY, GLU 63 GLY, VAL 69 ALA, ALA 73 LEU, LYS 78 GLU, LYS 80 ARG, VAL 84 ILE, PRO 91 LEU, LYS 195 GLU, VAL 196 GLU, SER 200 ARG or GLY, LEU 214 HIS, LEU 243 TYR, MET 253 TYR, LEU 268 ARG or GLN or PRO, THR 271 ILE, THR 275 ASN, and LEU 286 ARG wherein the surface resistance of the mutant lipase is increased compared to said natural lipase.

14. The mutant lipase according to claim 13 further comprising an additional substitution in SEQ ID NO:2 at the amino acid position MET 21.

15. A detergent composition including the mutant lipase of claim 1.

16. A detergent composition including the mutant lipase of claim 9.

17. A detergent composition including the mutant lipase of claim 12.

* * * * *